(12) United States Patent
Haas et al.

(10) Patent No.: US 6,503,513 B2
(45) Date of Patent: Jan. 7, 2003

(54) DIAGNOSTICS AND THERAPY OF DISEASES ASSOCIATED WITH HHV-8 INFECTIONS

(75) Inventors: Juergen Haas, Munich (DE); Elisabeth Kremmer, Freising (DE); Stefanie Kliche, Munich (DE)

(73) Assignee: GSF Forschungszentrum Fuer Umwelt und Gesundheit GmbH, Oberschleissheim (DE)

( * ) Notice: Subject to any disclaimer, the term of this patent is extended or adjusted under 35 U.S.C. 154(b) by 0 days.

(21) Appl. No.: 09/860,276

(22) Filed: May 16, 2001

(65) Prior Publication Data

US 2002/0090609 A1 Jul. 11, 2002

Related U.S. Application Data

(62) Division of application No. 09/291,803, filed on Apr. 14, 1999, now Pat. No. 6,319,667.

(30) Foreign Application Priority Data

Apr. 15, 1998 (DE) .......................... 198 16 732

(51) Int. Cl.[7] ........................ A61K 39/245; C12Q 1/70; G01N 33/53
(52) U.S. Cl. ................ 424/229.1; 424/204.1; 435/5; 435/7.1; 435/6; 530/300; 530/350; 536/23.72
(58) Field of Search .................. 435/5, 7.1, 6; 530/300, 530/350; 536/23.72; 424/204.1, 229.1

(56) References Cited

U.S. PATENT DOCUMENTS

5,861,240 A * 1/1999 Ganem et al. ................ 435/5

FOREIGN PATENT DOCUMENTS

WO    WO 97/31932    * 9/1997

OTHER PUBLICATIONS

Zhong et al., "Medical Sciences: Restricted expression of Kaposi sarcoma–associated herpesvirus (human herpesvirus 8) genes in Kapoi sarcoma," *Proc. Natl. Acad. Sci. USA*, vol. 93, pp. 6641–6646, (Jun. 1996).

* cited by examiner

*Primary Examiner*—Ali R. Salimi
(74) *Attorney, Agent, or Firm*—Townsend and Townsend and Crew, LLP (57) ABSTRACT

The present invention is directed to monoclonal antibodies capable of specifically binding to and recognizing an antigenic determinant (epitope) of the protein kaposin or a derivative therof, hybridoma cell lines producing said monoclonal antibodies, diagnostic systems for the detection of the presence of a kaposin protein or a derivative thereof as well as antibodies directed against the kaposin protein or a derivative thereof, methods for detection of the expression of kaposin protein or a derivative thereof in a biological sample, methods for the detection of antibodies directed against kaposin protein or a derivative thereof, uses of the monoclonal antibodies provided according to the invention and uses of the kaposin protein or a derivative thereof, each in diagnostics and therapy.

3 Claims, 4 Drawing Sheets

3a) Immunoblot

3b) Immunofluorescence (BCBL-1)

3c) Flow cytometry

FIG. 4

DIAGNOSTICS AND THERAPY OF DISEASES ASSOCIATED WITH HHV-8 INFECTIONS

"This application is a division of and claims the benefit of U.S. patent application Ser. No. 09/291,803, filed Apr. 14, 1999, now issued U.S. Pat. No. 6,319,667, the disclosure of which is incorporated by reference."

The present invention is directed to monoclonal antibodies capable of specifically recognizing an antigenic determinant (epitope) of the protein kaposin or a derivative therof and capable of binding thereto, hybridoma cell lines producing said monoclonal antibodies, diagnostic systems for the detection of the presence of a kaposin protein or a derivative thereof as well as antibodies directed against kaposin protein or a derivative thereof, methods for detection of the expression of kaposin protein or a derivative thereof in a biological sample, methods for the detection of antibodies directed against kaposin protein or a derivative thereof, uses of the monoclonal antibodies provided according to the invention and uses of kaposin protein or a derivative thereof, each in diagnostics and therapy.

BACKGROUND OF THE INVENTION

The human herpes virus 8 has been detected in all forms of Kaposi's sarcoma, in primary effusion lymphomas (PEL), in Castleman's disease, in angiosarcomas, in skin lesions of patients who underwent transplantations, in plasmacytomas, sarcoidosis as well as in healthy control individuals (Chang et al., 1994; Boshoff and Weiss, 1997). Seroepidemiological studies have shown that in northern and central Europe HHV-8 is substantially restricted to risk groups and that there are large differences with respect to geography and age.

Moreover, these studies were able to show that in patients with Kaposi's sarcomas a seroconversion for HHV-8 is detectable months to years prior to the diagnosis of Kaposi's sarcoma and that it is likely that HHV-8 is transferred primarily via sexual.contacts. To date, the clinical signs of a primary HHV-8 infection are unknown. Due to the detection of HHV-8 in almost 100% of all Kaposi's sarcomas, the correlation of the regional seroprevalence with the incidence of HHV-8 and the seroconversion prior to the appearance of Kaposi's sarcoma it is believed today that HHV-8 at least represents a co-factor in the tumorigenesis of KS. Up to now, the role of HHV-8 in the other diseases mentioned above is unclear and the question whether HHV-8 is involved in other so far unidentified diseases is still unanswered.

Taxonomically, on the basis of sequence homologies HHV-8 belongs to the gamma herpes virus sub-family and is closely related to EBV and *Herpesvirus saimiri*. The HHV-8 genome is 140 kb in size and is flanked by several repetitive sequences having a length of approximately 800 bp (Russo et al., 1996). HHV-8 codes for about 80 proteins, 10 of which show homology to cellular gene products (Neipel et al., 1997). Similar to all other herpes viruses, HHV-8 is able to cause a lytic infection which then becomes a latent infection. In the latent phase, at least two viral transcripts are expressed: a differentially spliced mRNA encoding the v-cyclin, v-flip and LANA proteins, as well as T0.7, a short RNA 0.7 kb in length and of up to now unknown function (Zhong et al., 1996). The viral transcript T0.7. is the most abundant of the RNAs expressed in the latent phase and has three open reading frames corresponding to 60, 35, and 47 amino acids.

So far, a HHV-8 infection has been detected by polymerase chain reaction using HHV-8-specific oligonucleotide primers. This direct method of detection has disadvantages in that it (i) requires at lot of effort and costs (about five to ten times the price of serological detection), (ii) is susceptible to false positive results due to contamination, (iii) detects only acute infections but not earlier ones, and (iv) detects only 50% of all (acutely) infected subjects if used on peripheral blood.

Figure 1A:
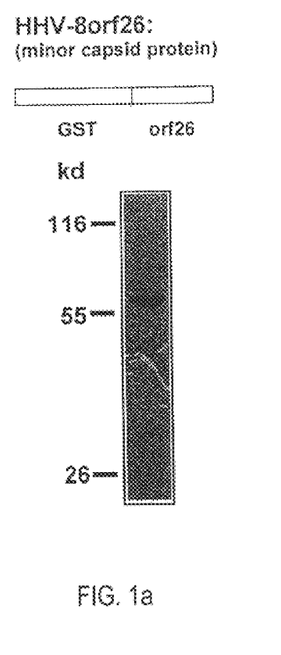
FIG. 1 is a chromatogram and a plot showing the reactivity of sera of patients suffering from Kaposi's sarcoma against recombinant minor capsid protein VP23.
Figure 1B:
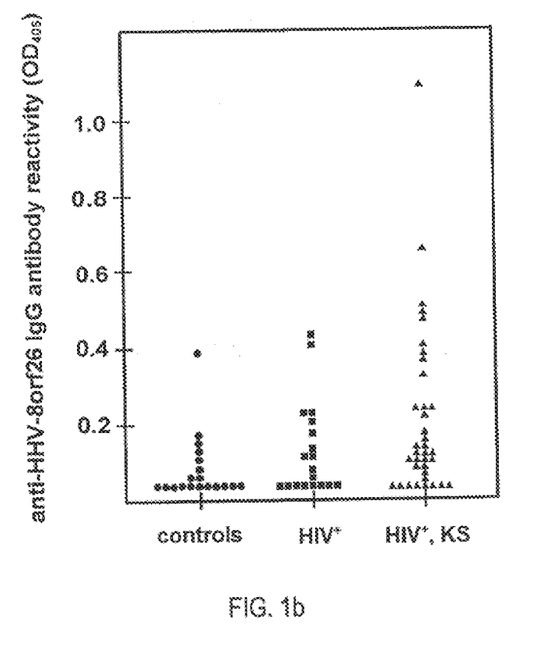

The serological detection methods developed so far are based on either the use of HHV-8-infected cell lines or on recombinant viral proteins. Assays detecting the antibodies directed against HHV-8 on HHV-8-positive cell lines by means of immunofluorescence have the disadvantages that (i) their reproducibility is low (i.a. because it is impossible to keep the culture conditions for the HHV-8 cell lines absolutely constant), (ii) their evaluation may not be performed by machine which makes them unsuitable for a larger number of tests, and (iii) it is in part difficult to exclude cross-reactions of antibodies against other viruses. A common problem of all of the assays based on recombinant viral proteins is their low sensitivity. This problem is based on the fact that antibodies are produced only against particular proteins of the virus and that different individuals may in part produce antibodies against different proteins. The viral proteins tested to date for their utility in serological diagnostics have a sensitivity of only between 30 and 80%. FIG. 1 exemplarily shows that antibodies against the minor capsid protein VP23 can be detected in only 30% of KS patients (FIG. 1). It is highly likely that the use of more than one viral protein is required in order to develop more sensitive assays.

Since with respect to its frequency Kaposi's sarcoma is in third place of the tumors occuring after an organ transplantation and according to current knowledge its occurence is closely associated to HHV-8 infection it may be expected that in the future organ donors and possibly also blood products will be tested for HHV-8 similar to e.g. the obligatory testing for HIV, hepatitis B and C which is performed today.

In part, the dignity of KS is highly variable. The KS which does not occur endemically is almost exclusively restricted to the immunodeficient patient and generally has a malignant course. It is treated by chemotherapy (such as liposomal doxorubicin), surgically or by means of radiotherapy with modest success. Retrospective studies indicate that the virostatics Foscarnet and Gancyclovir are effective. Larger prospective studies with regard to the effectivity of virostatics on KS have not been published to date. Also missing up to now is a uniform treatment schedule for the B cell lymphomas in which HHV-8 has been detected. Chemotherapeutic schedules have been widely used which were generally employed in the treatment of Non-Hodgekin lymphomas.

SUMMARY OF THE INVENTION

Therefore, it is an object of the present invention to provide novel means for the diagnostics and therapy of HHV-8 infections and of dieseases directly or indirectly caused by HHV-8.

According to the invention, this object has been achieved by the monoclonal antibodies characterized in claim 1 as well as by the hybridoma cell lines, diagnostic systems, methods of detection, and uses characterized in more detail in the dependent claims. Preferred embodiments of the invention are obvious from the dependent claims.

According to the invention, there are provided monoclonal antibodies specifically recognizing an epitope of the kaposin protein or a derivative thereof and binding to said epitope. An "epitope" according to the invention is intended to mean an antigenic determinant of kaposin peptide or protein or a derivative thereof which may be recognized by a monoclonal antibody and to which the monoclonal antibody can bind.

The derivative of kaposin peptide comprises an amino acid sequence of kaposin peptide formed by deletion, substitution, insertion, addition and/or chemical modification of one or more amino acid(s) provided that the antibody directed against an epitope of the derivative of kaposin peptide is useful for the specific detection of a HHV-8 infection.

The monoclonal antibody provided by the invention recognizes an epitope in the cytoplasmic region or the extracellular region of kaposin protein or a derivative thereof.

The monoclonal antibodies used in the present invention are specifically directed against an epitope of one of the following peptides:
(a) AIPPLVCLLA (SEQ ID NO:13); or
(b) QRGPVAFRTRVATG (SEQ ID NO:23).

A further embodiment also comprises the following sequence QRGPVAFRTRVA (SEQ ID NO:24), composed of the peptides 15 and 16 of Table 1.

In another embodiment of the invention the monoclonal antibody is directed against a peptide fragment (a derivative) thereof having a length of at least 5, at least 6, or at least 7 amino acids.

Figure 2:
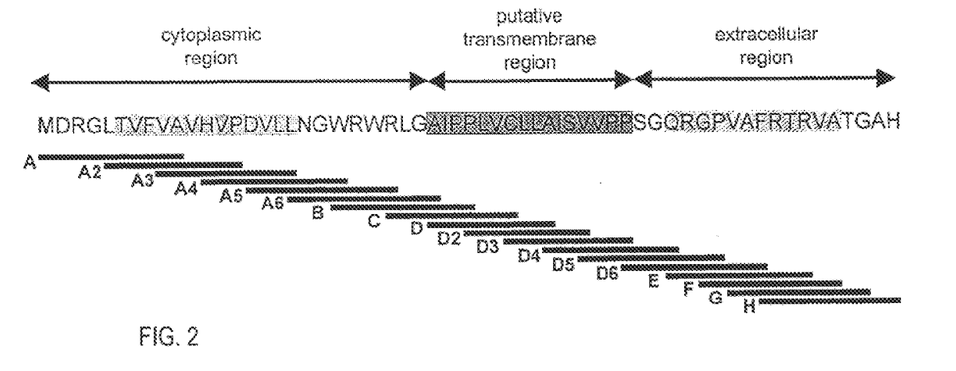
FIG. 2 shows the amino acid sequence of the first T0.7. RNA ORF ("kaposin").

"Kaposin protein" according to the invention is intended to mean a protein having the amino acid sequence shown in FIG. 2 (SEQ ID NO:1) or partial sequences of the protein (peptides). Comprised by the invention are also above mentioned peptides and derivatives thereof having an amino acid sequence formed by deletion, substitution, insertion, addition, and/or chemical modification of one or more amino acid(s) provided that the derivative is useful for the specific detection of a HHV-8 infection and/or provided that a monoclonal antibody may be directed against the derivative of kaposin peptide, useful for diagnostics and/or therapy of HHV-8 infections and diseases.

Also, the invention relates to hybridoma cell lines producing a monoclonal antibody as characterized in more detail hereinabove.

According to the invention, also diagnostic systems in the form of a kit are provided. These diagnostic systems are present in two embodiments.

In the first embodiment, the diagnostic system serves for the detection of a kaposin protein or a derivative thereof, as defined above. The diagnostic system contains at least a monoclonal antibody, as defined in more detail above, in a container. Typically, the kit systems comprise the antibody in labeled or unlabeled forms, reagents to perform the necessary incubations, and substrates or derivatizing agents which will be employed depending on the labeling used.

The detection of the presence or the expression, respectively, of kaposin protein or a derivative thereof in a biological sample may be performed for example as follows: The sample is contacted with a monoclonal antibody, as described abbove, under conditions such that the antibody is able to bind to an antigenic component of the sample; then, the proportion of antibody binding to the antigenic component in the sample is determined.

As the sample, for example a body liquid, an intact cell, a cellular extract, or a tissue will be used. The proportion of binding of the antibody may be for example determined by immunocytochemical or immunohistochemical staining.

In a second embodiment of the invention, the diagnostic system is designed to be capable of detecting monoclonal or polyclonal antibodies present in a sample, such as a body liquid, an intact cell, a cellular extract, or a tissue. For this purpose, a kaposin peptide or a derivative thereof, as defined above and in claim 1, is provided in an appropriate form in a suitable container, the protein or the derivative thereof being capable of undergoing a immunereaction with the monoclonal or polyclonal antibody to be detected. The sample is contacted with the kaposin peptide or a derivative thereof under conditions suitable to enable binding of the antibody present or presumed to be present in the sample directed against the kaposin peptide or a derivative thereof; furthermore, the proportion of binding of the antibody in the sample to the kaposin peptide of the derivative thereof is determined.

BRIEF DESCRIPTION OF THE FIGURES

FIG. 3 shows the data used in the detection of kaposin expression in the HHV-8+ cell line BCBL-1 using kap5C4 mab.

DETAILED DESCRIPTION OF THE INVENTION AND PREFERRED EMBODIMENTS

Thus, the methods of the present invention essentially comprise incubation of the sample to be tested with monoclonal antibodies, or, in the reverse the incubation of kaposin peptide thereof with a sample to be tested which is presumed to contain monoclonal antibodies or polyclonal antibodies directed against kaposin peptide or a derivative thereof. According to the invention, "incubation" may also refer to any other means of contacting sample material with antibodies. Many possible basic methods of performing such immunoassays to be applied are known. These methods comprise for example RIA, ELISA, precipitation methods, agglutination methods, complement-fixation methods, and immunofluorescence methods. The monoclonal antibodies or the kaposin peptide or a derivative thereof may be present in labeled form. The labels used in the preparation of labeled forms of the antibodies or proteins comprise groups which are directly detectable, such as radiolabels and fluorochromes, as well as groups such as enzymes which must be reacted or derivatized for detection. A radiolabel may be detected by any known method. An enzyme labeling may be detected by any calorimetric, spectrophotometric, fluoro-spectrophotometric or gasometric technique known per se. The enzyme is linked to the antibody via bridging molecules, such as carbodiimide, periodate, diisocyanate, glutaraldehyde. In these methods, many enzymes known per se may be employed. Examples are peroxidase, alkaline phosphatase, β-glucuronidase, β-D-glucosidase, β-D-galactosidase, urease, glucose oxidase plus peroxidase, galactose oxidase plus peroxidase, and acid phosphatase. Fluorescent materials which may be employed comprise for example fluorescein and its derivatives, rhodamine and its derivatives, auramine, luciferin, horse-radish peroxidase, alkaline phosphatase, lysozyme, and glucose-6-phosphate dehydrogenase. The antibodies may be bound to these labels by methods known per se. Examples for coupling agents are aldehydes, carbodiimides, dimaleimides, imidates, succinimides, to provide the antibodies with the above-described fluorescent, chemiluminescent and enzyme labels.

The antibodies and labeled antibodies and the peptides produced here may be used to detect diseases directly or indirectly caused by HHV-8, such as B cell lymphomas, in a patient and/or to monitor the status of the disease. For this purpose either qualitative or quantitative immunoassay methods may be employed. The assay techniques comprise direct and indirect detection procedures. If the sample contains for example Kaposi's sarcoma cells, the labeled antibody will bind to these cells. Following washing of the tissue or the cells to remove unbound labeled antibody the sample is examined for labeled immune complexes. In the indirect detection methods, the tissue or the cell sample or a body liquid is incubated with unlabeled monoclonal antibody. Then, the sample is treated with a labeled antibody directed against the monoclonal antibody, washed, and the presence of ternary complexes is examined.

For diagnostic purposes, the antibodies and also the kaposin peptides will be typically present in kit form.

Description of therapeutical uses of the antibodies In an in vivo therapy the present antibodies are administered in therapeutically effective amounts (i.e. amounts abolishing or alleviating the disease directly or indirectly caused by HHV-8) to a patient. This is generally done by the parenteral or intravenous route. The dose and the formulation are dependent on the nature of the disease to be treated and the patient.

The derivative of the kaposin peptide employed according to the invention or the derivative of the kaposin peptide to be detected according to the invention preferably comprises an amino acid sequence of the kaposin peptide formed by deletion, substitution, insertion, addition and/or chemical modification of one or more amino cid(s). However, the final product of a derivatization process of that type is always designed to enable a specific detection of a HHV-8 infection or a disease induced by HHV-8 infection.

In this invention, the kaposin peptide or its derivative each comprises an epitope in the cytoplasmic region and the extracellular region of kaposin protein or a derivative thereof. The peptides have the following amino acid sequence:
(a) AIPPLVCLLA (SEQ ID NO:13); or
(b) QRGPVAFRTRVATG (SEQ ID NO:23).
A further embodiment shows the following sequence: QRGPVAFRTRVA (SEQ ID NO:24).

The fragments of the kaposin peptides have a length of at least 5, at least 6 or at least 7 amino acids. The monoclonal antibodies provided according to the invention are directed against kaposin peptide or the derivatives of the kaposin peptides described in more detail above.

The present antibodies are employed in diagnostics and therapy of diseases caused directly or indirectly by infections with HHV-8. These include for example Kaposi's sarcoma, AIDS diseases and B cell lymphomas.

Also, the kaposin peptides provided by the invention or the derivatives of kaposin peptides characterized in more detail above are used in diagnostics and therapy of HHV-8 infections, AIDS diseases, Kaposi's sarcomas and B cell lymphomas.

In the following, the invention will be described in more detail with respect to Examples and the accompanying Figures. The Figures show:

FIG. 1: Reactivity of Sera of Patients Suffering from Kaposi's Sarcoma Against Recombinant Minor Capsid Protein VP23

(a) The minor capsid protein VP23 of HHV-8 was expressed as GST-tagged protein in *E. coli*, purified via affinity chromatography by glutathione sepharose and employed in an ELISA for the detection of anti-VP23 antibodies in patient sera. (b) Microtiter plates were coated with 1 μg of recombinant VP23 and blocked by PBS/0.1% Tween 20. The sera of 19 HIV-negative control donors, 19 HIV-positive individuals without KS and 36 HIV-negative patients with KS were pre-incubated with lyophilized *E.coli* and then incubated in a dilution of 1:50 for 2 hours at room temperature on the microtiter plate. After 4 washing steps, a peroxidase-conjugated secondary antibody and afterwards ABTS substrate were added. The sera of the HIV-positive KS patients showed a clear reactivity against VP23 (Wilcoxon test p<0.0024) but only about ⅓of the sera was higher than a cut-off of OD 0.2. Therefore, the assay may be hardly used for the detection of HHV-8 infection.

FIG. 2: Amino Acid Sequence of the First T0.7. RNA ORF ("Kaposin")

In the kaposin amino acid sequence (SEQ ID NO:1), the presumable transmembrane region (SEQ ID NO:3) (underlayed by dark box), the binding site of kap5C4 mab (SEQ ID NO:24) (underlayed by hatched box) and a second hydrophobic region (underlayed by light box) with so far unknown function have been indicated. The peptides used for epitope mapping (see also Table 1) are shown in the lower panel of the Figure. The cytoplasmic region (SEQ ID NO:2) and extracellular region (SEQ ID NO:4) are also indicated.

FIG. 3: Detection of Kaposin Expression in the HHV-8+ Cell Line BCBL-1 using kap5C4 mab (a) Detection of kaposin by Western Blot in uninduced HHV-8+ BCBL-1 cells but not in the EBV+ control cell line 721. (b) Detection of kaposin in fixed/permeabilized (upper panel) and unpermeabilized (lower panel) BCBL-1 cells by immunofluorescence and evaluation using a confocal laser microscope. In both of the left panels the cells shown by immunofluorescence on the right are shown by means of phase contrast photography. The uninduced BCBL-1 cells were first reacted with undiluted cell culture supernatant of kap5C4 hybridoma and then with a Cy-3-labeled secondary antibody. (c) Evaluation of the kap5C4-stained cells shown above in the flow cytometer (bold curve). As the positive control, an antibody W6/32 directed against MHC class 1 was used (dotted curve). In the negative control, incubation was performed only with the secondary antibody (plain curve).

Figure 4:
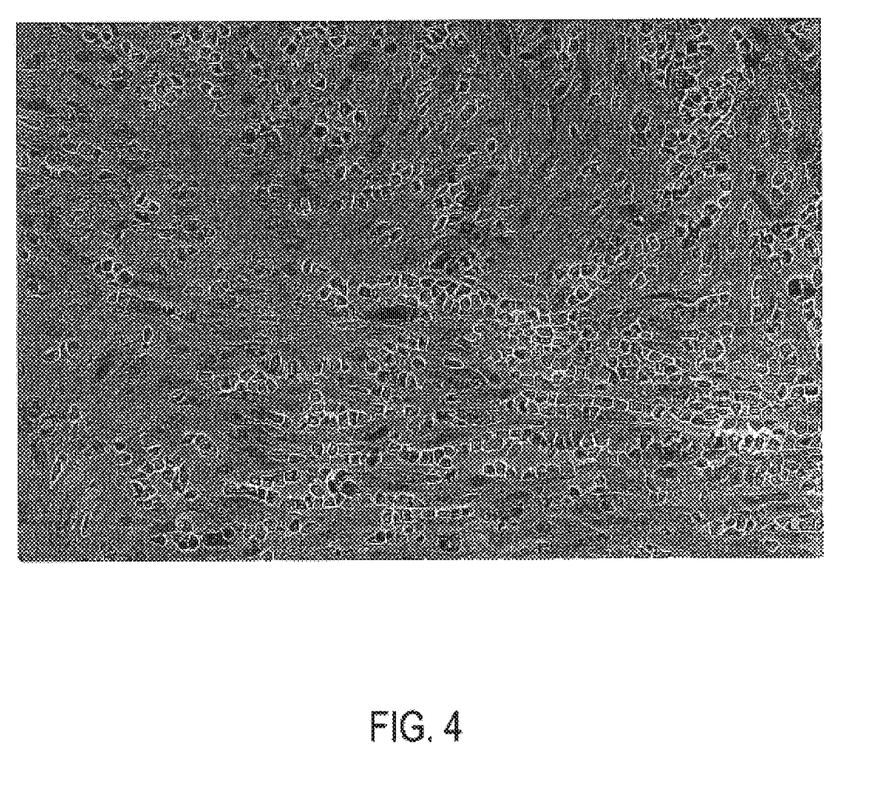
FIG. 4 shows the immunohistological staining of KS tissue with mabs against lytic HHV-8 VP23 protein.

FIG. 4: Immunohistological Staining of KS Tissue with mabs Against Lytic HHV-8 VP23 Protein The formaline-fixed and paraffin-embedded thin section of a Kaposi's sarcoma was stained with vp4G2 mab against HHV-8 VP23. First, the section was cleared from paraffin by boiling and afterwards incubated with a 1:10 dilution of vp4G2 mab. Bound antibodies were detected using the EnVision™ system (Dako, Hamburg).

Cells infected by HHV-8 in a latent manner express at least 2 viral transcripts. The most abundant viral mRNA in the latent phase, T0.7, has a length of 0.7 kb and three short open reading frames (ORFs). Up to now, no translation of any of these ORFs has been demonstrated. The first ORF has a length corresponding to only 60 amino acids. In the bulk of the literature only two transmembrane proteins are described which are smaller than 14 kd (ponticulin and L-selectin), and this is the reason why it was unclear whether T0.7. is translated at all or if it like the T1.1/nut-1 transcript (equally encoding an ORF of 62 amino acids in length) discovered at the same time has a regulatory function. The patent application is based on the following studies of the first ORF of T0.7, called "kaposin":

1. Expression of the First ORF of T0.7. Transcript ("Kaposin") in HHV-8-Infected Cells The applicant was able to show that the first open reading frame of the T0.7. transcript, "kaposin", is indeed translated in HHV-8-infected cells. The sequence of the first ORF was expressed in E. coli in the form of a GST (glutathione-S-transferase) fusion protein and purified using affinity chromatography. The recombinant fusion protein was used for the preparation of monoclonal antibodies (mab). For this purpose, Lou/C rats were immunized and the spleen cells were fused with the myeloma cell line P3C63Ag8.653 according to standard techniques. The antibodies were screened with recombinant fusion protein by ELISA and rescreened with recombinant GST. The kap5C4 mab recognizes recombinant kaposin fusion protein but not GST in the Western blot. By means of peptide mapping, kap5C4 mab was found to recognize the peptide sequence QRGPVAFR-TRVA (SEQ ID NO:24) at the C-terminus (FIG. 2 and Tab. 1). In cell lysates of HHV-8-infected cell lines a protein could be identified by Western blot, immunoprecipitation and following surface biotinylation having a length of 6 kd predicted on the basis of the sequence (FIG. 3a).

2. Expression of Kaposin on the Cell Surface

It was shown by immunofluorescence that kaposin is expressed on the surface of HHV-8-infected cell lines (FIGS. 3b and c). The FIG. 3b shows that kaposin is recognized by kap5C4 mab in fixed and permeabilized BCBL-1 cells (HHV-8-positive, EBV-negative cell line established from a primary effusion lymphoma). Further, the Figure shows that kaposin is also detectable on unpermeabilized cells and therefore must be localized on the cell surface. The immunofluorescence shows staining on the periphery typical for cell surface molecules. The FIG. 3c shows a flow-cytometric analysis of BCBL-1 cells stained with kap5C4 or a control antibody against MHC class 1. It is obvious that the expression with kap5C4 mab is clearly positive about one log higher than the negative control. Since kap5C4 recognizes the C-terminus of kaposin the results must be interpreted in a way that kaposin is a type II protein (N-terminus is localized in the cytoplasm).

3. Expression of Kaposin in the Majority of HHV-8-Infected Cells

Lytic proteins such as the VP23 minor capsid protein studied by the applicant are expressed by HHV-8+ cell lines only after induction with phorbol esters and/or n-butyrate. By immunohistology, in most of the KS tissues only a very small portion of spindle cells is positive with vp4G2 mab against VP23 (FIG. 4). In contrast, HHV-8+ cell lines express kaposin in a constitutive manner without previous induction. Depending on the cell line and staining method the percentage of positive cells varies between 10 and more than 80%. Also by immunohistology, the number of cells stained by kap5C4 mab is much greater than the vp4G2-positive cells. Presumably, with a more sensitive staining method a major portion of all spindle cells would be positive for kaposin.

4. Recognition of kaposin by Sera of KS patients and KS Risk Groups

It was shown by Western blot that kaposin fusion protein is recognized by sera of KS patients and of HIV-infected individuals without KS, respectively. It was demonstrated that a higher percentage (approx. 80%) of the sera of the HIV-infected (risk group: homosexuals) reacted with kaposin as compared to other viral proteins/peptides. This may indicate that kaposin as a latent viral membrane protein is more suitable for the detection of early infections than lytic proteins. By peptide-ELISA a rough mapping was performed to determine the epitope recognized by these sera. It was demonstrated that a hydrophobic peptide having the amino acid sequence AIPPLVCLLA (SEQ ID NO:13) was recognized by most of the sera (Tab. 1).

Advantages Over the Prior Art and Potential Utilization

As outlined above, the detection methods used to date of a HHV-8 infection suffer from many disadvantages. At the moment no therapy specifically directed against HHV-8 exists. The viral protein kaposin described herein has the following advantages over the viral proteins used so far:

1. Expression on the cell surface
2. Expression in a majority of HHV-8-infected cells
3. Kaposin is the latent HHV-8 protein showing the best expression
4. No homologies to other proteins (also viral) are known ot date The potential uses become obvious from the function of kaposin as a reliable infection or tumor marker which according to present data is well expressed by a majority of HHV-8-infected cells. Therefore, kaposin is useful for the development of (i) novel diagnostic methods for the detection of HHV-8 infection and (ii) of therapeutics specifically directed against HHV-8. In the field of diagnostics for example the use of recombinant kaposin in ELISAs or Western blots for serological detection or the use of mab against kaposin for the detection of HHV-8-infected cells in immunohistology may be contemplated. A reliable serological assay has the following possibilities of application:

Diagnosis of HHV-8 infection;

prognostic marker for the development of a KS sarcoma in HIV-infected individuals, patients after transplantation and immunosuppressed patients;

course parameter in the therapy of Kaposi's sarcoma;

diagnosis of certain B cell lymphomas;

course parameter in the therapy of HHV-8+ B cell lymphomas; possibly in the diagnosis of so far unknown tumors (e.g. also so-called "secondary tumors" following organ transplantations) and possibly other diseases so far not connected with HHV-8;

course parameter in these HHV-8-associated diseases.

In principle, also a therapeutic utilization of kaposin may be contemplated, e.g. if bispecific antibodies are used which by cross-linking of HHV-8+ tumor cells with T lymphocytes may lead to targeted activation of the immune response and thus to an elimination of the tumor cells. Since up to now the mechanism by which HHV-8-infected cells can be transformed is unknown, kaposin as a latent protein may be involved as the causative agent. If this should prove to be true a therapeutical intervention leading to a blockage of kaposin may be of therapeutical benefit.

Cell Lines

The cell lines BCBL-1 (HHV-8+, EBV−) (kindly provided by Don Ganem; UCSF, USA) and 721 (EBV+ lymphoblastoid cell line) used were passaged in RPMI (Life Technologies, Paisley, UK) supplemented with 20% of heat-inactivated fetal calf serum, 100 IU/ml of penicillin, 100 μg/ml of streptomycin, 2 mM L-glutamine, and 0.05 mM 2-mercaptoethanol (Sigma, St. Louis, USA).

Preparation of Recombinant HHV-8 Fusion Proteins

The sequence of the first ORF of T0.7. was amplified from extracted DNA of BCBL-1 cells by PCR, cloned into pGEX-4T vector (Pharmacia, Uppsala, Sweden), expressed in E. coli as a GST (glutathione-S-transferase) fusion protein and purified by affinity chromatography according to standard techniques (Ausubel et al., 1992).

Preparation of Monoclonal Antibodies Against Kaposin

The monoclonal antibodies were prepared according to standard methods as described previously (Kremmer et al., 1995). Lou/C rats were immunized in intervals of 3 weeks with the recombinant fusion protein and trehalose dimycolate/monophosphoryl lipid A/squalene/Tween 80 (Antibody Multiplier ABM-S, Linaris, Bettingen, Germany) as the adjuvant for a total of three times. Spleen cells of the immunized rats were fused with P3C63Ag8.653 myeloma cell line and the hybridoma supernatants were tested by means of ELISA (enzyme-linked immunosorbent assay) on mikrotiter plates coated with the recombinant protein in a concentration of 1 µg/well. The supernatants were incubated for 1 hour and the bound antibodies detected using a peroxidase-conjugated secondary antibody against rat immunoglobulin. Afterwards, o-phenylene diamine was added as the substrate and the absorbance measured in an ELISA reader (Tecan, Reading, UK). In total, antibody kap5C4 was cloned twice.

Western Blotting

Cell lysates of unstimulated BCBL-1 and 721 cells were separated on a 18% SDS PAGE and blotted onto nitrocellulose (Schleicher and Schuell, Dassel, Germany). Afterwards, the blot was blocked with 5% milk powder (Merck, Darmstadt, Germany) in TBS (tris-balanced saline)/0.02% Tween-20 and incubated with kap5C4 mab. Following three washing steps in TBS/0.02% Tween-20 the blot was incubated for one hour with alkaline phosphatase-conjugated secondary antibody (Dianova, Hamburg, Germany) in a dilution of 1:1000, again washed and finally incubated with Western Blue (Promega, Madison, USA) according to the manufacturer's instructions.

Immunofluorescence

For intracellular staining, the uninduced BCBL-1 cells were fixed in aceton and permeabilized with 0.2% saponine. Untreated BCBL-1 cells were used for surface staining. The BCBL-1 cells were first incubated with undiluted kap5C4 hybridoma cell culture supernatant and then with a Cy-3-labeled secondary antibody (Sigma, St. Louis, USA). For analysis, the cells were fixed on poly-L-lysine-coated slides (Marienfeld, Bad Mergentheim, Germany) and analyzed by Leica TNT confocal laser microscope (Leica, Bensheim, Germany). For control in flow cytometry W6/32 mab against MHC class I was used as the primary antibody. Analysis was conducted on a FACSscalibur flow cytometer (Becton Dickinson, Mountain View, USA).

ELISA

The microtiter plates were coated with 1 µg of recombinant VP23 and blocked by PBS/0.1% Tween-20. Sera of 19 HIV-negative control donors, 19 HIV-positive individuals without KS and 36 HIV-negative patients with KS were pre-incubated with lyophilized *E. coli* and afterwards incubated in a dilution of 1:50 for two hours at room temperature on the microtiter plate. After 4 washing steps a secondary peroxidase-conjugated antibody followed by ABTS substrate (Boehringer, Mannheim, Germany) was added.

Peptides were used to perform the peptide ELISA which were linked at their N termini to a SGSG spacer and were biotinylated. A stock solution of each of the peptides (concentration of 1 µmole/ml in 100% DMSO) was diluted 1:400 in PBS/5% Tween-20 and bound to streptavidin-coated microtiter plates. Following an incubation with a dilution of 1:200 of kap5C4 mab hybridoma supernatant and 1:50 of KS patient serum, respectively, a peroxidase-conjugated secondary antibody against rat IgG (kap5C4) or human IgG was used in a dilution of 1:10.000. After reaction with the secondary antibody the microtiter plates were incubated with ABTS substrate and then measured with an ELISA reader at a wavelength of 492 nm. To identify epitopes against which the antibodies in HHV-8-infected persons are directed a serum pool of HIV-positive patients (<10) suffering from Kaposi's sarcoma was used.

Immunohistology

First, the section was cleared of paraffin and then incubated with vp4G2 mab in a dilution of 1:10. Bound antibodies were detected using the EnVision™ system (Dako, Hamburg, Germany).

REFERENCES

Ausubel, F. M., R. Brent, R. E. Kingston, D. D. Moore, J. G. Seidmann, J. A. Smith, and K. Struhl, eds. (1992). Current protocols in molecular biology. John Wiley and Sons, New York Boshoff, C. and Weiss, R. A. (1997). Aetiology of Kaposi's sarcoma: current understanding and implications for therapy. Mol. Med. Today 488–494.

Chang, Y., Cesarman, E., Pessin, M. S., Lee, F., Culpepper, J., Knowles, D. M., and Moore, P. S. (1994). Identification of herpesvirus-like DNA sequences in AIDS-associated Kaposi's sarcoma. Science 266,1865–1869.

Kremmer, E., Kranz, B. R., Hille, A., Klein, K., Eulitz, M., Hoffmann-Fezer, G., Feiden, W., Hermann, K., Delecluse, H.-J., Delsol, G., Bornkamm, G. W., Mueller-Lantzsch, N., and Graesser, F. A. (1995). Rat monoclonal antibodies diffentiating between the Epstein-Barr Virus nuclear antigens 2A (EBNA 2A) and 2B (EBNA 2B). Virology 208, 336–342.

Neipel, F., Albrecht, J. -C., and Fleckenstein, B. (1997). Cell-homologous genes in the Kaposi's sarcoma-associated rhadinovirus human herpesvirus 8: determinants of its pathogenicity? J. Virol. 71, 4187–4192.

Russo, J. J., Bohenzky, R. A., Chien, M. -C., Chen, J., Yan, M., Maddalena, D., Parry, J. P., Peruzzi, D., Edelman, I. S., Chang, Y., and Moore, P. (1996). Nucleotide sequence of the Kaposi's sarcoma-associated herpesvirus (HHV8). Proc. Natl. Acad. Sci. USA 93, 14862–14867.

Zhong, W., Wang, H., Herndier, B., and Ganem, D. (1996). Restricted expression of Kaposi sarcoma-associated herpesvirus (human herpesvirus 8) genes in Kaposi sarcoma. Proc. Natl. Acad. Sci. USA 93, 6641–6646.

TABLE 1

Epitope mapping of kap5C4 monoclonal antibody and of KS patients

| Name | Peptide Sequence (N→C) | Reactivity kap5C4 mab | Reactivity KS patient sera | SEQ ID NO: |
|---|---|---|---|---|
| 1. K12A | MDRGLTVFVA | — | — | SEQ ID NO:5 |
| 2. K12A2 | LTVFVAVHVP | — | — | SEQ ID NO:6 |
| 3. K12A3 | VAVHVPDVLL | — | — | SEQ ID NO:7 |
| 4. K12A4 | HVPDVLLNGW | — | — | SEQ ID NO:8 |
| 5. K12A5 | DVLLNGWRWR | — | — | SEQ ID NO:9 |
| 6. K12A6 | LNGWRWRLGA | — | — | SEQ ID NO:10 |

TABLE 1-continued

Epitope mapping of kap5C4 monoclonal antibody and of KS patients

| Name | Peptide Sequence (N→C) | Reactivity kap5C4 mab | Reactivity KS patient sera | SEQ ID NO: |
|---|---|---|---|---|
| 7. K12B | WRWRLGAIPP | − | − | SEQ ID NO:11 |
| 8. K12C | RLGAIPPLVC | − | − | SEQ ID NO:12 |
| 9. K12D | AIPPLVCLLA | − | +++ | SEQ ID NO:13 |
| 10. K12D2 | PLVCLLAISV | − | − | SEQ ID NO:14 |
| 11. K12D3 | CLLAISVVPP | − | − | SEQ ID NO:15 |
| 12. K12D4 | AISVVPPSGQ | − | − | SEQ ID NO:16 |
| 13. K12D5 | VVPPSGQRGP | − | − | SEQ ID NO:17 |
| 14. K12D6 | PSGQRGPVAF | − | − | SEQ ID NO:18 |
| 15. K12E | QRGPVAFRTR | +++ | − | SEQ ID NO:19 |
| 16. K12F | GPVAFRTRVA | +++ | − | SEQ ID NO:20 |
| 17. K12G | VAFRTRVATG | − | − | SEQ ID NO:21 |
| 18. K12H | FRTRVATGAH | − | − | SEQ ID NO:22 |

The peptides indicated are linked at their N-terminus to a SGSG spacer (SEQ ID NO:25) and biotinylated. A stock solution of each of the peptides (concentration of 1 µmole/ml in 100% DMSO) was diluted 1:400 in PBS/5% Tween-20 and bound to streptavidin-coated microtiter plates. Following an incubation with a dilution of 1:200 of kap5C4 mab hybridoma supernatant and 1:50 of KS patient serum, respectively, a peroxidase-conjugated secondary antibody against rat IgG (kap5C4) or human IgG was used in a dilution of 1:10.000. After reaction with the secondary antibody the microtiter plates were incubated with ABTS substrate and then measured with an ELISA reader at a wavelength of 492 nm. To identify epitopes against which the antibodies in HHV-8-infected persons are directed a serum pool of HIV-positive patients (<10) suffering from Kaposi's sarcoma was used.

What is claimed is:

1. Kaposin peptide selected from the group consisting of:
   (a) AIPPLVCLLA (SEQ ID NO:13),
   (b) QRGPVAFRTRVATG (SEQ ID NO:23), and
   (c) derivatives of (a) and (b) that contain at least 5 contiguous amino acids and that are formed by deletion, substitution, insertion, addition, and/or chemical modification of an amino acid of peptides (a) or (b).

2. Method for the detection of antibodies directed against the kaposin protein or an epitope selected from the group consisting of:
   (a) AIPPLVCLLA (SEQ ID NO:13),
   (b) QRGPVAFRTRVATG (SEQ ID NO:23), and
   (c) derivatives of (a) and (b) that contain at least 5 contiguous amino acids and that are formed by deletion, substitution, insertion, addition, and/or chemical modification of an amino acid of peptides (a) or (b),
   in a biological sample, said method comprising contacting said sample with said kaposin protein or a peptide selected from said group for binding of said antibodies present in said sample, and determining the proportion of binding of said antibodies in said sample to said kaposin protein or said peptide selected from said group.

3. Method according to claim 2 wherein said sample is a liquid, an intact cell, a cellular extract or a tissue.

* * * * *

SEQUENCE LISTING

```
<160> NUMBER OF SEQ ID NOS: 25

<210> SEQ ID NO 1
<211> LENGTH: 60
<212> TYPE: PRT
<213> ORGANISM: human herpesvirus 8
<220> FEATURE:
<223> OTHER INFORMATION: kaposin - first T0.7 RNA ORF
<221> NAME/KEY: DOMAIN
<222> LOCATION: (1)..(26)
<223> OTHER INFORMATION: cytoplasmic region
<221> NAME/KEY: TRANSMEM
<222> LOCATION: (27)..(42)
<223> OTHER INFORMATION: putative transmembrane region
<221> NAME/KEY: DOMAIN
<222> LOCATION: (43)..(60)
<223> OTHER INFORMATION: extracellular region

<400> SEQUENCE: 1

Met Asp Arg Gly Leu Thr Val Phe Val Ala Val His Val Pro Asp Val
 1               5                  10                  15

Leu Leu Asn Gly Trp Arg Trp Arg Leu Gly Ala Ile Pro Pro Leu Val
                20                  25                  30

Cys Leu Leu Ala Ile Ser Val Val Pro Pro Ser Gly Gln Arg Gly Pro
            35                  40                  45

Val Ala Phe Arg Thr Arg Val Ala Thr Gly Ala His
        50                  55                  60

<210> SEQ ID NO 2
<211> LENGTH: 26
<212> TYPE: PRT
<213> ORGANISM: human herpesvirus 8
<220> FEATURE:
<221> NAME/KEY: DOMAIN
<222> LOCATION: (1)..(26)
<223> OTHER INFORMATION: cytoplasmic region
```

<400> SEQUENCE: 2

Met Asp Arg Gly Leu Thr Val Phe Val Ala Val His Val Pro Asp Val
 1               5                  10                  15

Leu Leu Asn Gly Trp Arg Trp Arg Leu Gly
            20                  25

<210> SEQ ID NO 3
<211> LENGTH: 16
<212> TYPE: PRT
<213> ORGANISM: human herpesvirus 8
<220> FEATURE:
<221> NAME/KEY: TRANSMEM
<222> LOCATION: (1)..(16)
<223> OTHER INFORMATION: putative transmembrane region

<400> SEQUENCE: 3

Ala Ile Pro Pro Leu Val Cys Leu Leu Ala Ile Ser Val Val Pro Pro
 1               5                  10                  15

<210> SEQ ID NO 4
<211> LENGTH: 18
<212> TYPE: PRT
<213> ORGANISM: human herpesvirus 8
<220> FEATURE:
<221> NAME/KEY: DOMAIN
<222> LOCATION: (1)..(18)
<223> OTHER INFORMATION: extracellular region

<400> SEQUENCE: 4

Ser Gly Gln Arg Gly Pro Val Ala Phe Arg Thr Arg Val Ala Thr Gly
 1               5                  10                  15

Ala His

<210> SEQ ID NO 5
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12A

<400> SEQUENCE: 5

Met Asp Arg Gly Leu Thr Val Phe Val Ala
 1               5                  10

<210> SEQ ID NO 6
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12A2

<400> SEQUENCE: 6

Leu Thr Val Phe Val Ala Val His Val Pro
 1               5                  10

<210> SEQ ID NO 7
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)

<223> OTHER INFORMATION: K12A3

<400> SEQUENCE: 7

Val Ala Val His Val Pro Asp Val Leu Leu
 1               5                  10

<210> SEQ ID NO 8
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12A4

<400> SEQUENCE: 8

His Val Pro Asp Val Leu Leu Asn Gly Trp
 1               5                  10

<210> SEQ ID NO 9
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12A5

<400> SEQUENCE: 9

Asp Val Leu Leu Asn Gly Trp Arg Trp Arg
 1               5                  10

<210> SEQ ID NO 10
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12A6

<400> SEQUENCE: 10

Leu Asn Gly Trp Arg Trp Arg Leu Gly Ala
 1               5                  10

<210> SEQ ID NO 11
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12B

<400> SEQUENCE: 11

Trp Arg Trp Arg Leu Gly Ala Ile Pro Pro
 1               5                  10

<210> SEQ ID NO 12
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12C

<400> SEQUENCE: 12

-continued

```
Arg Leu Gly Ala Ile Pro Pro Leu Val Cys
 1               5                  10
```

<210> SEQ ID NO 13
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12D

<400> SEQUENCE: 13

```
Ala Ile Pro Pro Leu Val Cys Leu Leu Ala
 1               5                  10
```

<210> SEQ ID NO 14
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12D2

<400> SEQUENCE: 14

```
Pro Leu Val Cys Leu Leu Ala Ile Ser Val
 1               5                  10
```

<210> SEQ ID NO 15
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12D3

<400> SEQUENCE: 15

```
Cys Leu Leu Ala Ile Ser Val Val Pro Pro
 1               5                  10
```

<210> SEQ ID NO 16
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12D4

<400> SEQUENCE: 16

```
Ala Ile Ser Val Val Pro Pro Ser Gly Gln
 1               5                  10
```

<210> SEQ ID NO 17
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12D5

<400> SEQUENCE: 17

```
Val Val Pro Pro Ser Gly Gln Arg Gly Pro
 1               5                  10
```

```
<210> SEQ ID NO 18
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12D6

<400> SEQUENCE: 18

Pro Ser Gly Gln Arg Gly Pro Val Ala Phe
 1               5                  10

<210> SEQ ID NO 19
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12E

<400> SEQUENCE: 19

Gln Arg Gly Pro Val Ala Phe Arg Thr Arg
 1               5                  10

<210> SEQ ID NO 20
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12F

<400> SEQUENCE: 20

Gly Pro Val Ala Phe Arg Thr Arg Val Ala
 1               5                  10

<210> SEQ ID NO 21
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12G

<400> SEQUENCE: 21

Val Ala Phe Arg Thr Arg Val Ala Thr Gly
 1               5                  10

<210> SEQ ID NO 22
<211> LENGTH: 10
<212> TYPE: PRT
<213> ORGANISM: human herpesvirus 8
<220> FEATURE:
<221> NAME/KEY: PEPTIDE
<222> LOCATION: (1)..(10)
<223> OTHER INFORMATION: K12H

<400> SEQUENCE: 22

Phe Arg Thr Arg Val Ala Thr Gly Ala His
 1               5                  10

<210> SEQ ID NO 23
<211> LENGTH: 14
<212> TYPE: PRT
<213> ORGANISM: human herpesvirus 8
```

```
<400> SEQUENCE: 23

Gln Arg Gly Pro Val Ala Phe Arg Thr Arg Val Ala Thr Gly
  1               5                  10

<210> SEQ ID NO 24
<211> LENGTH: 12
<212> TYPE: PRT
<213> ORGANISM: human herpesvirus 8

<400> SEQUENCE: 24

Gln Arg Gly Pro Val Ala Phe Arg Thr Arg Val Ala
  1               5                  10

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:spacer

<400> SEQUENCE: 25

Ser Gly Ser Gly
  1
```